United States Patent [19]

Worms et al.

[11] Patent Number: 5,033,243
[45] Date of Patent: Jul. 23, 1991

[54] PORTABLE SHELTER

[76] Inventors: Gerard W. Worms, Box 64, Pilger, Saskatchewan, Canada, S0K 3G0; Percy A. Eggerman, Box 242, Watson, Saskatchewan, Canada, S0K 4V0

[21] Appl. No.: 542,955
[22] Filed: Jun. 25, 1990
[51] Int. Cl.[5] .............................................. B65D 7/02
[52] U.S. Cl. ............................................ 52/245; 52/80; 52/82
[58] Field of Search ................... 52/79.1, 79.4, 80, 81, 52/82, 236.2, 245

[56] References Cited

U.S. PATENT DOCUMENTS

| 4,112,644 | 9/1978 | Allen | 52/80 |
|---|---|---|---|
| 4,665,664 | 5/1987 | Knight | 52/81 |
| 4,784,172 | 11/1988 | Yacoboni | 52/80 |
| 4,910,928 | 3/1990 | Cellar, Jr. | 52/82 |
| 4,965,970 | 10/1990 | Nania | 52/82 |

Primary Examiner—Richard E. Chilcot, Jr.
Assistant Examiner—Joanne C. Downs
Attorney, Agent, or Firm—Murray E. Thrift; Stanley G. Ade; Adrian D. Battison

[57] ABSTRACT

A portable shelter especially for leafcutter bee nest, consists of six identical molded plastic panels and a molded roof cap. The panels are fastened together using molded in place tabs and pins to form a circular wall that is domed at the top and capped at the center with the roof cap, also fastened in place with integral pins and holes in a peripheral flange.

15 Claims, 2 Drawing Sheets

PORTABLE SHELTER

FIELD OF THE INVENTION

The present invention relates to portable shelters and more particularly to a lightweight portable shelter that is especially, although not exclusively, useful in sheltering leafcutter bee nests.

BACKGROUND

Leafcutter bees are housed in nests in agricultural fields for pollination purposes. The nests themselves are usually wooden boxes or surrounds housing perforated blocks in which the bees actually nest. These nests are placed out in agricultural fields during the growing season and are usually sheltered from the weather with a temporary shelter, often fabricated from wood and plastic film.

The present invention is concerned with a novel portable shelter that can be used for sheltering leafcutter bee nests and other purposes.

SUMMARY

According to one aspect of the present invention there is provided a portable shelter comprising a plurality of substantially identical panels of synthetic plastic material, each panel having opposite side edges and including a lower panel portion comprising a substantially cylindrical segment, an upper panel portion sloping upwardly from the lower panel portion, first coupling means along one side edge of the panel, second coupling means along the opposite side edge of the panel, the first coupling means of each panel being engageable with the second coupling means of another one of the panels, whereby the panels may be secured together into a peripheral wall with a converging upper section, and a roof unit comprising a peripheral flange adapted to engage over upper edges of the assembled panels.

According to another aspect of the present invention there is provided a portable shelter comprising six panels of synthetic plastic material, each having a lower panel section in the shape of a cylindrical segment subtending a 60° centre angle, an intermediate panel section in the shape of a frusto-conical segment extending upwardly and inwardly from the lower panel section, an upper panel section in the shape of a frusto-conical segment with a slope greater than that of the intermediate panel section and extending upwardly and inwardly from the intermediate panel section, a top flange extending upwardly from the upper panel section in the shape of a cylindrical segment, a bottom flange of an L-shape section extending inwardly and upwardly from a bottom edge of the lower panel section, each panel having three reinforcing channels molded therein, including two outer channels extending from the bottom of the lower panel section to the top of the upper panel section adjacent opposite side edges of the panel, and an inner channel extending from the bottom to the top of the lower panel section and being offset towards one of the side edges, a door opening in one of the panels, between the inner channel and the furthest therefrom of the outer channels, locking tabs formed along one edge of each panel, each having an opening therethrough, and pins formed along the opposite edge of each panel engaging the openings in the locking tabs of the adjacent panel, a cap comprising a cylindrical cover flange engaged over the top flanges of the panels, an outer annular cover section extending inwardly from the cover flange, an inner, circular cover section spaced above and concentric with the outer cover section, an upstanding annular wall joining the inner and outer cover sections, and a plurality of ventilation openings in the annular wall, at least one pin formed in the top flange of each panel and projecting outwardly therefrom, and holes in the cover flange engaging with the pins.

The shelter is readily assembled. It is light in weight and can therefore easily be transported. Bee nests can be arranged around the inside of the shelter, supported off the ground on the bottom flange.

BRIEF DESCRIPTION OF THE DRAWINGS

In the accompanying drawings, which illustrate an exemplary embodiment of the present invention.

DETAILED DESCRIPTION

Referring to the accompanying drawings, there is illustrated a shelter 10 having an annular peripheral wall 12 with a door 14 in the wall and a roof cap 16 closing the top of the shelter.

Figure 2:
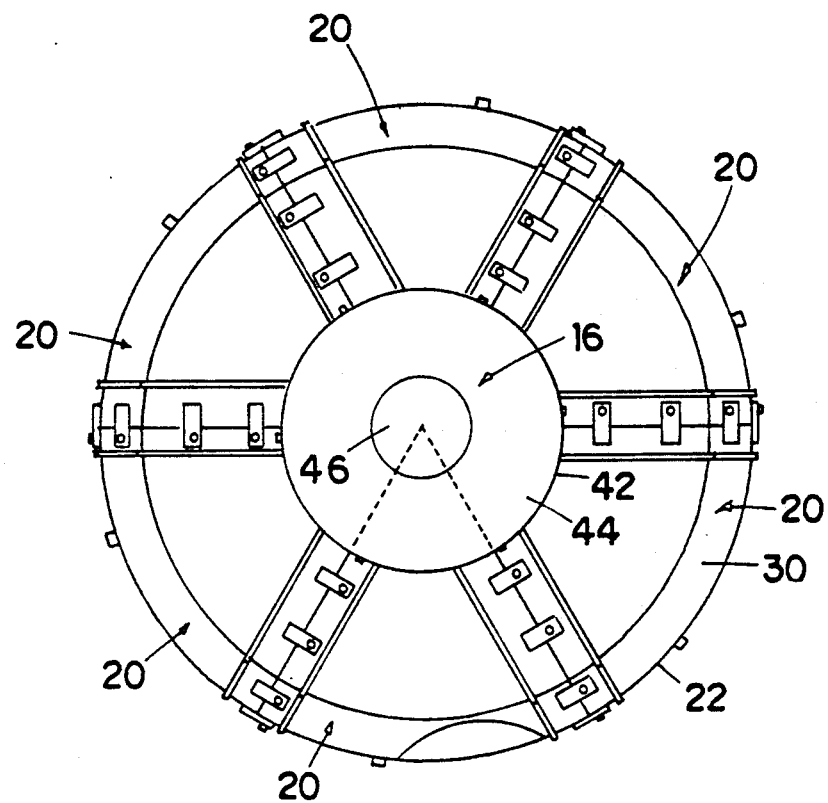
FIG. 2 is a plan view of the shelter FIG. 1.

As illustrated in FIG. 2, the shelter is composed of six panels 20 which are joined together to form the peripheral wall, and the roof cap 16.

Figure 1:
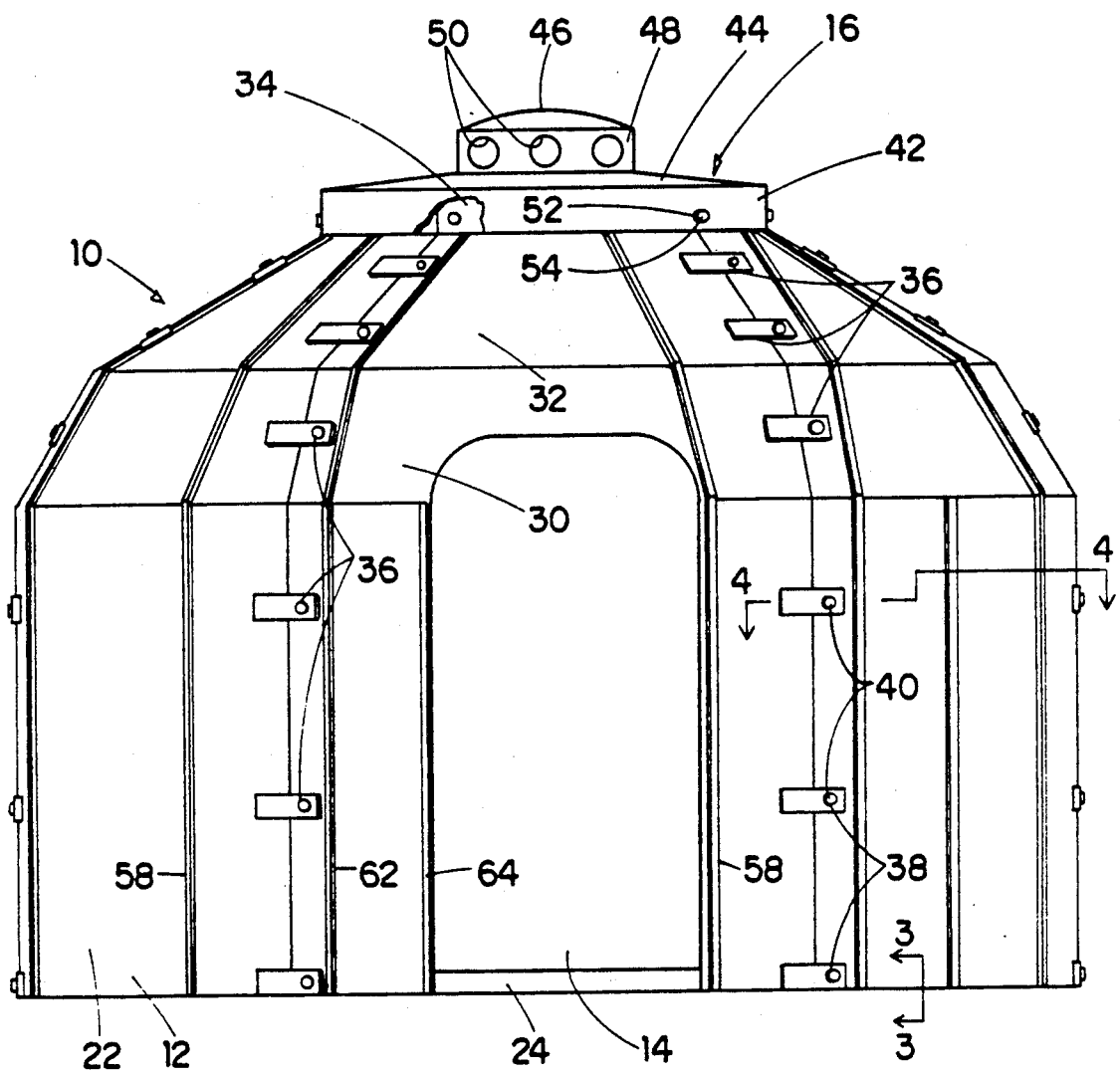
FIG. 1 is an elevation of a shelter according to the present invention.
Figure 3:
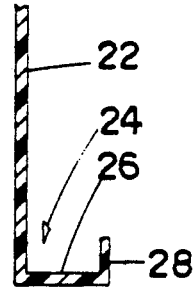
FIG. 3 is a vertical section along section 3—3 of FIG. 1.
Figure 4:
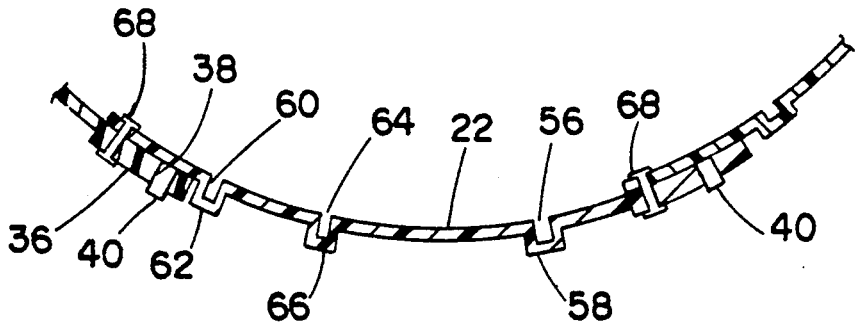
FIG. 4 is a horizontal section along line 4—4 of FIG. 1.

The construction of a single panel 20 is most clearly illustrated in FIGS. 1, 3 and 4. The panel has a lower section 22 in the form of a cylindrical segment subtending a centre angle of 60° (see FIG. 2). At the bottom of the lower section is a bottom flange 24 that is L-shaped with a base section 26 extending inwardly from the bottom of the panel lower section 22 and a vertical section 28 that extends upwardly from inner edge of the base section 26. At the top of the lower panel section 22 is an intermediate panel section 30 in the form of a frusto-conical segment. Above the intermediate panel section is an upper panel section 32, also in the form of a frusto-conical segment, but with a greater slope than the intermediate panel section. At the top of the panel is a top flange 34 in the form of a vertically extending cylindrical section.

Spaced along one side of each panel are fastening tabs 36. These are rectangular tabs that project from the side of the panel to overlay the adjacent panel when the two are assembled. Each tab has an opening 38 formed in its projecting end. Spaced along the opposite edge of each panel are pins 40 that are positioned to engage in the holes 38 in the tabs 36 of an adjacent panel thus securing the panels together.

The roof of the shelter includes a cylindrical cover flange 42 that fits over the cylinder formed by the top flanges 34 of the assembled panels 20. Extending from the top edge of the cover flange 42 is a frusto-conical outer cover section 44. At the centre of the roof cap is an inner cover section 46 joined to the outer cover section by an annular wall 48. A series of large vent openings 50 are formed in the wall 48.

Six holes 52 are formed in the cover flange 42 at uniform spacing around the flange to engage a similar series of pins 54 on the top flanges 34 of the wall panels. This secures the roof cap in place.

As illustrated most particularly in FIGS. 1 and 4, each panel 20 is molded with a channel 56 adjacent one edge extending from the bottom of the lower panel section 22 to the top of the upper panel section 32. On the outside of the panel this channel defines a reinforcing rib 58. A similar channel 60 extends along the panel from the bottom of the lower section 22 to the top of the upper panels 32 adjacent the opposite side edge. This defines a reinforcing rib 62 on the outside of the panel like rib 58. A third reinforcing channel 64-rib 66 is formed in the panel. This rib and channel structure extends from the bottom of the lower section 22 to its top and is offset towards one side of the panel. This offset allows a door opening to be cut in any panel without severing any of the reinforcing ribs, particularly as shown in FIG. 1.

The panels 20 are molded as a unit with the tabs 36 and pins 40, 54. The roof cap is likewise molded as a single piece. Consequently, the unit is quite inexpensively manufactured of two separate moldings containing all of the necessary structure. The only modification that is needed to any of the molded units is the cutting of a door in one panel, which is relatively straight forward and can be done either at the factory or by the purchaser of the unit.

Once the unit has been assembled it may be desired to augment the fastening of the pins and tabs with fasteners 68 through the tabs and the overlapping parts of the adjacent panels as illustrated in FIG. 4. The fasteners used may be hollow rivets or other fasteners.

In the use of the shelter for housing leafcutter bee nests, the nest blocks are supported on the bottom flange 24, leaning against the side wall of the shelter, all around the inside of the shelter.

While one particular embodiment of the present invention has been described in the foregoing, it is to be understood that other embodiments are possible within the scope of the invention. The invention is to be considered limited solely by the scope of the appended claims.

We claim:

1. A portable shelter comprising a plurality of substantially identical unitary, rigid panels of synthetic plastic material, each panel having opposite side edges and including a lower panel portion comprising a substantially cylindrical segment, an upper panel portion integral with the lower panel portion and sloping upwardly from the lower panel portion, first coupling means integral with the panel and extending along one side edge of the panel, second coupling means integral with the panel and extending along the opposite side edge of the panel, the first coupling means of each panel being engageable with the second coupling means of another one of the side panels, whereby the panels may be secured together into a peripheral wall with a converging upper section having a central opening therein, and a roof unit comprising a cap of a size larger than the central opening and a peripheral flange depending form the cap and adapted to engage over upper edges of the assembled panels.

2. A portable shelter comprising six panels of synthetic plastic material, each having a lower panel section in the shape of a cylindrical segment subtending a 60° centre angle, an intermediate panel section in the shape of a frusto-conical segment extending upwardly and inwardly from the lower panel section, an upper panel section in the shape of a frusto-conical segment with a slope greater than that of the intermediate panel section and extending upwardly and inwardly from the intermediate panel section, a top flange extending upwardly from the upper panel section in the shape of a cylindrical segment, a bottom flange of an L-shape section extending inwardly and upwardly from a bottom edge of the lower panel section, each panel having three reinforcing channels molded therein, including two outer channels extending from the bottom of the lower panel section to the top of the upper panel section adjacent opposite side edges of the panel, and an inner channel extending from the bottom to the top of the lower panel section and being offset towards one of the side edges, a door opening in one of the panels, between the inner channel and the furthest therefrom of the outer channels, locking tabs formed along one edge of each panel, each having an opening therethrough, and pins formed along the opposite edge of each panel engaging the openings in the locking tabs of the adjacent panel, a cap comprising a cylindrical cover flange engaged over the top flanges of the panels, an outer annular cover section extending inwardly from the cover flange, an inner, circular cover section spaced above and concentric with the outer cover section, an upstanding annular wall joining the inner and outer cover sections, and a plurality of ventilation openings in the annular wall, at least one pin formed in the top flange of each panel and projecting outwardly therefrom, and holes in the cover flange engaging with the pins.

3. A portable shelter according to claim 1 wherein each upper panel portion comprises an intermediate panel section extending upwardly and inwardly from the lower panel portion and an upper panel section with a slope greater than that of the intermediate panel section and extending upwardly and inwardly from the intermediate panel section.

4. A portable shelter according to claim 1 wherein the shelter comprises six of said panels.

5. A portable shelter according to claim 1 wherein the first coupling means comprises locking tabs formed along said one edge of the panel.

6. A portable shelter according to claim 5 wherein the second coupling means comprise pins integrally formed with the panel along the said opposite edge of the panel, the pins being engageable with the locking tabs.

7. A portable shelter according to claim 6 including openings through the locking tabs, the pins being engageable through respective ones of the openings.

8. A portable shelter according to claim 7 including at least one further pin formed in each panel adjacent the upper edge thereof and holes formed in the peripheral flange of the roof unit for engaging the further pins adjacent the upper edges of the panels.

9. A portable shelter according to claim 1 wherein each panel comprises a bottom flange of L-shaped section.

10. A portable shelter according to claim 9 wherein the bottom flange extends inwardly and upwardly from the bottom edge of the lower panel portion.

11. A portable shelter according to claim 1 wherein each panel comprises a plurality of reinforcing channels extending vertically therealong.

12. A portable shelter according to claim 11 including a reinforcing channel adjacent each side edge of panel.

13. A portable shelter according to claim 12 including a further reinforcing channel extending from the bottom to the top of the lower panel portion.

14. A portable shelter according to claim 13 wherein the further reinforcing channel is offset towards one of the side edges.

15. A portable shelter according to claim 1 wherein the cap comprises a plurality of ventilation openings therein.

* * * * *